US006251682B1

(12) United States Patent
Rosell et al.

(10) Patent No.: US 6,251,682 B1
(45) Date of Patent: Jun. 26, 2001

(54) METHOD AND MARKERS FOR PROGNOSTICATING EFFICACY OF ANTICANCER AGENTS

(75) Inventors: Rafael Rosell; Mariano Monzó, both of Barcelona (ES)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/323,971

(22) Filed: Jun. 2, 1999

(51) Int. Cl.[7] .......................... G01N 33/00; G01N 33/48; C07H 21/04; C12Q 1/68; C12P 19/34
(52) U.S. Cl. ............................ 436/94; 436/63; 436/64; 536/23.1; 435/6; 435/91.1; 435/91.2
(58) Field of Search .............................. 435/6, 91.1, 91.2, 435/440; 436/94; 536/23.1, 24.3, 24.33, 25.3; 702/20

(56) References Cited

FOREIGN PATENT DOCUMENTS

WO 00/7152
A2    11/2000  (WO) .

OTHER PUBLICATIONS

Dumontet C., et al. "Resistance mechanisms in human sarcoma mutants dervied by single-step exposure to paclitaxel", *Cancer Research*, 1996 56(5) 1091–1097.

Monzo et al., Beta –tubulin gene mutations induce taxol chemoresistance in non–small cell lung cancer. Proceedings of the American Association for Cancer Research 38, 251 (#1689), 1997.*

Giannakakou et al., Paclitaxel –resistant human overian cancer cells have mutant beta–tubulins that exhibit impaired paclitaxel–driven polymerization. J. Biol. Chem. 272, 17118–17125, 1997.*

Ohta et al., Characterization of a taxol–resistant human small–cell lung cancer cell line. Jpn. J. Cancer Res. 85, 290–297, 1994.*

Chang et al., "Phase II Study of Taxol, Merbarone, and Piroxantrone in Stage IV Non–Small–Cell Lung Cancer: The Eastern Cooperative Oncology Group Results", J. Natl Cancer Inst. 85:388–394, 1993.

Kavallaris et al., "Taxol–resistant Epithelial Ovarian Tumors Are Associated with Altered Expression of Specific β–Tubulin Isotypes", J. Clin, Invest. 100:1282–1293, 1997.

Murphy et al., "Phase II Study of Taxol in Patients with Untreated Advanced Non–Small–Cell Lung Cancer", J. Natl Cancer Inst. 85:384–388, 1993.

Zaman et al., "The human multidrug resistance–associated protein MRP is a plasma membrane drug–efflux pump", Proc. Natl Acad. Sci. USA 91:8882–8826 1994.

* cited by examiner

*Primary Examiner*—Ethan Whisenant
*Assistant Examiner*—Frank Lu
(74) *Attorney, Agent, or Firm*—Licata & Tyrrell P.C.

(57) ABSTRACT

Methods and markers for prognosticating the efficacy of anti-cancer agents in patients suffering from cancer by detection of mutant tubulin genes are provided.

2 Claims, No Drawings

METHOD AND MARKERS FOR PROGNOSTICATING EFFICACY OF ANTICANCER AGENTS

BACKGROUND OF THE INVENTION

Microtubules are a major filament of the cytoskeleton and are involved in various biologic phenomena including mitosis, cell shape determination, cell locomotion and movement of intracellular organelles. Tubulin is one of the major microtubular components. Polymerization and depolymerization of tubulin regulate microtubular dynamics. Microtubules are considered one of the most important molecular targets for cancer chemotherapy.

Antimitotic agents which disrupt microtubules can be classified into two categories based on mechanism of action. These are the vinca alkaloids such as estramustine, rhizoxin and E7010, which inhibit microtubule polymerization, and taxanes such as paclitaxel and docetaxel which promote polymerization of microtubules and enhance microtubule stability.

The anti-mitotic anticancer agent paclitaxel is active against solid tumors. Paclitaxel is a microtubule-disrupting agent that primarily targets tubulin. In the absence of guanosine triphosphate (GTP), paclitaxel induces polymerization and stabilizes tubulin to cold- or calcium-induced microtubule depolymerization, thereby blocking cell cycle in the M phase. Tubulin is a heterodimer that consists of the alpha- and beta-tubulin subunits that form the microtubule.

Clinical trials with taxanes such as paclitaxel and docetaxel have revealed these agents to be effective against several cancers which were advanced or resistant to other anticancer drugs, especially breast cancer, ovarian cancers and non small cell lung carcinoma (NSCLC). With respect to NSCLC, a number of randomized clinical trials have demonstrated that survival in patients with advanced stage III or IV NSCLC can be prolonged with paclitaxel. Preliminary studies with paclitaxel showed response rates of 21% and 24% and an impressive 1-year survival rate of 45% in one trial (Chang et al. J. Natl Cancer Inst. 85:388–394, 1993; and Murphy et al. J. Natl Cancer Inst. 85:384–388, 1993). Paclitaxel is now often used in combination with other cytotoxic drugs including cisplatin and carboplatin in patients with NSCLC.

However, the acquisition of drug-resistant tumor cells is still a major problem in the medical treatment of malignant disease. The hydrophobic nature of drugs such as paclitaxel is known to induce overexpression of the MDR1 gene (Horwitz et al. Monogr J. Natl Cancer Inst. 15:55–61, 1993). However, paclitaxel resistant human lung cancer cells selected in the presence of low levels of paclitaxel do not express MDR1 (Kavallaris et al. J. Clin, Invest. 100:1282–1293, 1997). Further, cells expressing high levels of the multidrug resistance (MDP)-associated protein MRP display no or low resistance to paclitaxel (Zamas et al. Proc. Natl Acad. Sci. USA 91:8822–8826 1994).

It has now been found that mechanisms of drug resistance to anti-cancer agents such as paclitaxel in cancer are related to mutations in the beta-tubulin gene which affect microtubule dynamics.

SUMMARY OF THE INVENTION

An object of the present invention is to provide prognostic markers for efficacy of anti-cancer agents in patients suffering from cancer, wherein the prognostic markers comprise mutant tubulin genes.

Another object of the present invention is to provide a method of prognosticating the efficacy of anti-cancer agents in a patient suffering from cancer which comprises obtaining a biological sample from the patient and analyzing the sample for mutant tubulin genes, wherein the presence of mutant tubulin genes is indicative of a resistance to antimitotic anti-cancer agents such as taxanes.

DETAILED DESCRIPTION OF THE INVENTION

Point mutations in the tubulin gene have now been linked with paclitaxel resistance in human tumors in the clinical setting. A group of patients without beta-tubulin gene mutations had a 39.4% response rate with a 10 month median survival time, and 1-year, 3-year and 5-year survival rates of 33.3%, 12.1% and 3%, respectively. In contrast, patients with beta-tubulin mutations showed no response to paclitaxel treatment and poor survival.

Specifically, forty-nine patients with non small cell lung carcinomas were examined. Forty-eight patients underwent biopsy before starting chemotherapy to obtain tissue for histologic diagnosis. A portion of the tumor specimen was also processed for genetic analysis. One patient had a biopsy performed after receiving paclitaxel. Forty-Three patients were treated with paclitaxel 210 mg/m$^2$ in a 3-hour infusion every 9 weeks. Six patients were treated with paclitaxel 200 mg/m$^2$ in a 24-hour infusion every 3 weeks. After three courses of paclitaxel, a decision was made regarding continuing treatment. All tumor responses were submitted to a peer-review process by two independent radiologists. Responders received up to a maximum of 10 courses. Responses were graded as complete if all evidence of disease disappeared on follow-up computed tomography scans. A partial response was defined as more than a 50% reduction in the sum of products at the largest perpendicular diameter of all indicator lesions. Survival was calculated from the date of first treatment to the most recent follow-up contact or to the date of death and included all patients in the study. Median follow-up from the time of treatment for the entire series of patients was 7 months (range 1 to 67 months).

The genomic DNA of exons 1 through 4 of the beta-tubulin gene was sequenced in all 49 patients. Findings from this analysis provided evidence for mutations. To distinguish somatin mutations from rare germline variants, variations in normal control DNA for each patient were also determined. Normal control DNA was obtained either: from nonepithelial normal tissue in archival paraffin-embedded biopsy samples; by isolation of DNA from distant normal nonepithelial, archival paraffin blocks other than the biopsy samples; or in six patients, by venipuncture and isolation of lymphocyte DNA. This analysis showed that patients' tumors contained true somatic mutations when matched with normal control DNA. Somatic mutations are shown in Table 1. Of the 19 somatic mutations identified in 16 patients, 13 were missense mutations, one was a single base-pair insertion, three were 1 base pair deletions and 2 were nonsense mutations. This analysis showed that 16 patients (33%; 95% CI, 20.7% to 45.3%) had beta-tubulin mutations.

There were no differences in baseline characteristics, including performance status and stage, in patients with and without beta-tubulin mutations. However, none of the patients with beta-tubulin mutations attained an objective response; one had stable disease and 15 had progressive disease. In contrast, of the remaining 33 patients without beta-tubulin mutations (including one patient who had a beta-tubulin polymorphism), 13 had partial or complete response (39.4%; 95% CI, 22.8% to 56%; p=0.01). Median survival for the 16 patients with beta-tubulin mutations was 3 months (95% CI, 2 to 3.9 months), whereas for the 33 patients with no beta-tubulin mutations, median survival was 10 months (95% CI, 7.9 to 12.1 months, p=0.0001). A set of monoclonal antibodies to detect and discriminate tubulin isotypes I, II and III showed no differences in histopathologic data, clinical data, or survival.

All patients with beta-tubulin mutations were chemotherapy naive, whereas in the group of patients with tubulin mutations, three North American patients had been unsuccessfully treated with cisplatin. Although one patient (Case A1 in Table 1) with beta-tubulin mutations survived for 23 months, the individual did not attain even a partial response. No second-line chemotherapy was foreseen for nonresponders, although 6 of the 14 patients with stage IIIB received radiotherapy after completion of the study.

being effective against the tumor, thereby decreasing the progression of the tumor and increasing the survival time of the patient. Biological samples which can be screened for these mutations are samples containing DNA. Examples include, but are not limited to, tumor biopsy samples and blood or serum samples obtained from the patient. Mutations in tubulin genes can be detected in these samples in accordance with well known methods including, but not limited to, those described herein.

The following nonlimiting examples are provided to further illustrate the present invention.

EXAMPLES

Example 1

Patients and DNA Extraction

Tumor specimens were analyzed from 49 patients with stage IIIB or IV NSCLC submitted for paclitaxel treatment (43 Spanish patients from three Spanish Centers and six

TABLE 1

Beta-Tubulin Mutations Found in Non Small Cell Lung Carcinoma Patients

| Patient/ Stage | Exon | Codon | Nucleotide change | Amino acid substitution | Mutant Type | Follow-up (months) | Status |
| --- | --- | --- | --- | --- | --- | --- | --- |
| M5/IV | 4 | 245 | CAG→AAG | Gln→Lys | transversion | 1 | DOD |
|  |  | 147 | ATG→AT | −1G frameshift | deletion |  |  |
| V9/IV | 4 | 245 | CTC→CTCC | +1C frameshift | insertion | 3 | DOD |
| B15/IV | 4 | 245 | CAG→GAG | Gln→Glu | transversion | 5 | DOD |
| A4/IV | 4 | 250 | CTC→CGC | Leu→Arg | transversion | 9 | DOD |
| M6/IV | 4 | 245 | CAG→GAG | Gln→Glu | transversion | 6 | DOD |
| M7/IIIB | 4 | 243 | CCT→TCT | Pro→Ser | transition | 3 | DOD |
| A7/IV | 4 | 235 | TGT→GGT | Cys→Gly | transversion | 2 | DOD |
|  |  | 147 | ATG→AT | −1G frameshift | deletion |  |  |
| B71/IV | 4 | 131 | CAG→AAG | Gln→Lys | transversion | 6 | DOD |
|  |  | 183 | TAC→TAA | Tyr-Stop | nonsense |  |  |
| B10/IIIB | 4 | 131 | CAG→AAG | Gln→Lys | transversion | 1 | DOD |
| AB/IV | 4 | 147 | ATG→AT | −1G frameshift | deletion | 2 | DOD |
| V1/IIIB | 4 | 150 | GTC→ATC | Val→Ile | transition | 1 | DOD |
| B2/IV | 4 | 183 | TAC→TAA | Tyr-Stop | nonsense | 4 | DOD |
| A1/IV | 4 | 180 | GTC→ATC | Val→Ile | transition | 23 | DOD |
| M3/IIIB | 4 | 127 | TGT→TTT | Cys→Phe | transversion | 1 | DOD |
| V6/IV | 4 | 260 | TTC→GTC | Phe→Val | transversion | 3 | DOD |
| V4/IV | 1 | 4 | ATC→ACC | Ile→Thr | transition | 3 | DOD |
| B16/IV | 1 | 11 | CAA→CAG | Glu→Glu | polymorphism | +36 | AWD |

DOD = died of disease
AWD = alive with disease

As demonstrated by these patients, the presence or absence of mutant tubulin genes, and in particular mutant beta-tubulin genes in a patient suffering from cancer can be used to prognosticate the efficacy of anti-mitotic anti-cancer agents, and in particular taxanes including, but not limited to, paclitaxel and docetaxel, in the treatment of the cancer in the patient. Thus, mutant beta-tubulin genes serve as prognostic markers for efficacy of anti-cancer agents in patients suffering from cancer. Efficacy of anti-cancer agents can be prognosticated in a patient suffering from cancer by obtaining a biological sample from the patient and then analyzing the sample for the presence or absence of mutant tubulin genes. In a preferred embodiment, the sample is analyzed for the presence of mutant beta-tubulin genes. The presence of mutant tubulin genes, and in particular mutant beta-tubulin genes, in the biological sample of the patient is indicative of a resistance of the tumor to anti-mitotic anti-cancer agents such as taxanes. Accordingly, other treatment regimes should be selected for these patients. The absence of mutant tubulin genes in the biological sample of the patient is indicative of anti-mitotic anti-cancer agents such as taxanes North American patients from the M.D. Anderson Cancer Center in Houston, Tex.). Of the six North American patients, three had received no prior treatment. The remaining three were treated unsuccessfully with cisplatin. Only one specimen was a tumor biopsy taken after the start of paclitaxel treatment, and normal tissue from the same patient was used as its control. Genomic DNAs were extracted from paraffin-embedded specimens, incubated in 10 mmol/L Tris, pH 8.1, 2.5 mmol/L $MgCl_2$, 50 mmol/L $KCl_2$, 0.5% TWEEN 20 (monolaurate polyoxyethylenesorbitan) and 1 mg/ml proteinase K. The mixture was then phenol-chloroform extracted, ethanol precipitated, vacuum dried and resuspended in $H_2O$.

For this polymerase chain reaction, different pairs of oligonucleotides were designed to amplify specific regions of the beta-tubulin gene (Genbank Accession No. J00314) that code for the GTP- and paclitaxel-binding sites. The samples were denatured at 95° for 5 minutes and then subjected to 35 cycles of denaturing for 1 minute at 95° C., annealing for 1 minute at various temperatures, and extension for 2 minutes at 72° C., followed by a final period of extension at 72° C. for 5 minutes. The products were separated by electrophoresis in agarose gels and visualized with ethidium bromide staining under ultraviolet light.

Example 2

DNA Sequencing

All DNA samples were also examined by automatic DNA cycle sequencing. Primers and primer dimers contained in the PCR-amplified products were removed using S300 HOUR Sephacryl microcolamine (Pharmacia Biotec, Uppsala, Sweden). Purified PCR products were used as a template in a cyclic sequencing reaction. Following this reaction, 4 µl of stop solution containing formamide and dextran blue was added, and the mixture was denatured at 95° C. for 3 minutes before loading into a prewarmed, denaturing, 6% polyacrylamide-3 mol/l urea gel on an ALF-express DNA sequencer. Samples were run at 40W for 2 to 3 hours and the sequencing data obtained were compared with the wild-type beta-tubulin sequences. Independent PCR products derived from each genomic DNA sample were analyzed at least twice.

Example 3

Immunofluorescence

Paraffin sections of tumor blocks were deparaffinized with xylene, rehydrated and washed for 10 minutes in tri-buffered saline (TBS). The slides were blocked with 2% BSA in TBS (TBS-BSA) for 30 minutes and washed three times with 0.02% TWEEN-20 in TBS (TBS-TWEEN). Primary monoclonal antibodies, anti I-II and III beta-tubulin isotypes (Sigma, St. Louis, Mo.) were diluted 1:400 in TBS-BSA and incubated overnight at 4° C. in a humid chamber, followed by extensive washing with TBS-TWEEN. The secondary antibody, a goat antibody to mouse immunoglobulin coupled to fluorescein (Dako, Denmark, Copenhagen), was diluted 1:200 in PBS-BSA and incubated for 30 minutes in a dark and humid chamber. The slides were then washed and mounted with cytofluoromedium (Sigma).

What is claimed is:

1. A method of prognosticating efficacy of anti-mitotic anti-cancer agents in a patient suffering from cancer comprising:

(a) obtaining a biological sample from the patient; and (b) analyzing the sample for mutant beta-tubulin genes with a mutation located in exon 1 or 4 of beta-tubulin gene, wherein the presence of said mutant beta-tubulin genes is indicative of the efficacy of anti-mitotic anti-cancer agents in the patient, wherein the anti-mitotic anti-cancer agents promote polymerization of microtubules and enhance microtubule stability.

2. A prognostic marker for efficacy of anti-mitotic anti-cancer agents in patients suffering from cancer comprising a mutant beta-tubulin gene with a mutation located in exon 1 or 4 of beta-tubulin gene, wherein the anti-mitotic anti-cancer agents promote polymerization of microtubules and enhance microtubule stability.

* * * * *